United States Patent
Vallittu et al.

(10) Patent No.: US 7,354,969 B2
(45) Date of Patent: Apr. 8, 2008

(54) DENTAL AND MEDICAL POLYMER COMPOSITES AND COMPOSITIONS

(75) Inventors: Pekka Vallittu, Kuusisto (FI); Lippo Lassila, Turku (FI); Mikael Skrifvars, Pitea (SE); Eeva Viljanen, Turku (FI); Antti Yli-Urpo, Littoinen (FI)

(73) Assignee: Stick Tech OY, Turko (FI)

( * ) Notice: Subject to any disclaimer, the term of this patent is extended or adjusted under 35 U.S.C. 154(b) by 412 days.

(21) Appl. No.: 10/467,080

(22) PCT Filed: Feb. 6, 2002

(86) PCT No.: PCT/FI02/00087

§ 371 (c)(1),
(2), (4) Date: Jan. 7, 2004

(87) PCT Pub. No.: WO02/062901

PCT Pub. Date: Aug. 15, 2002

(65) Prior Publication Data

US 2004/0097627 A1    May 20, 2004

(30) Foreign Application Priority Data

Feb. 6, 2001 (FI) .................................. 20010222

(51) Int. Cl.
  *C08L 51/06* (2006.01)
  *C08K 3/04* (2006.01)
  *C08K 3/40* (2006.01)

(52) U.S. Cl. ............ 524/504; 524/437; 524/494; 523/113; 977/DIG. 1

(58) Field of Classification Search ........... 523/113; 524/437, 494, 504
See application file for complete search history.

(56) References Cited

U.S. PATENT DOCUMENTS

| 4,267,097 A | * | 5/1981 | Michl et al. ............... 524/786 |
| 5,418,301 A | | 5/1995 | Hult et al. |
| 5,834,118 A | | 11/1998 | Ranby et al. |
| 5,886,064 A | | 3/1999 | Rheinberger et al. |
| 6,335,413 B1 | | 1/2002 | Zech et al. |
| 6,664,315 B2 | * | 12/2003 | Tomalia et al. ............. 523/218 |
| 6,712,997 B2 | * | 3/2004 | Won et al. .................. 252/503 |

FOREIGN PATENT DOCUMENTS

| EP | 0 716 103 | 5/1999 |
| EP | 0 948 956 | 10/1999 |
| WO | WO 93/18079 | 9/1993 |
| WO | WO 96/25911 | 8/1996 |
| WO | WO 98/24831 | 6/1998 |
| WO | WO 98/36729 | 8/1998 |
| WO | WO 99/09934 | 3/1999 |
| WO | WO 99/17716 | 4/1999 |
| WO | WO 99/45890 | 9/1999 |

* cited by examiner

*Primary Examiner*—Tae H Yoon
(74) *Attorney, Agent, or Firm*—Young & Thompson

(57) ABSTRACT

The invention relates to polymerizable multifunctional polymer composites and compositions, which are suitable for dental and medical applications, such as dental prostheses, filling materials, implants and the like. It also relates to a method for the manufacture of such polymerizable multifunctional polymer composites and compositions, and to the use of the multifunctional polymer composites and compositions in dental and medical applications. A multifunctional polymer composite or composition is manufactured from 30-99 wt % of a monomer mixture containing 30-99 wt % of a dendrimer or a combination of dendrimers and 1-70 wt % of a reactive solvent or a combination of reactive solvents, and 0.1-70 wt % of a nanofiller or a combination of nanofillers.

15 Claims, 1 Drawing Sheet

DENTAL AND MEDICAL POLYMER COMPOSITES AND COMPOSITIONS

Figure 1:
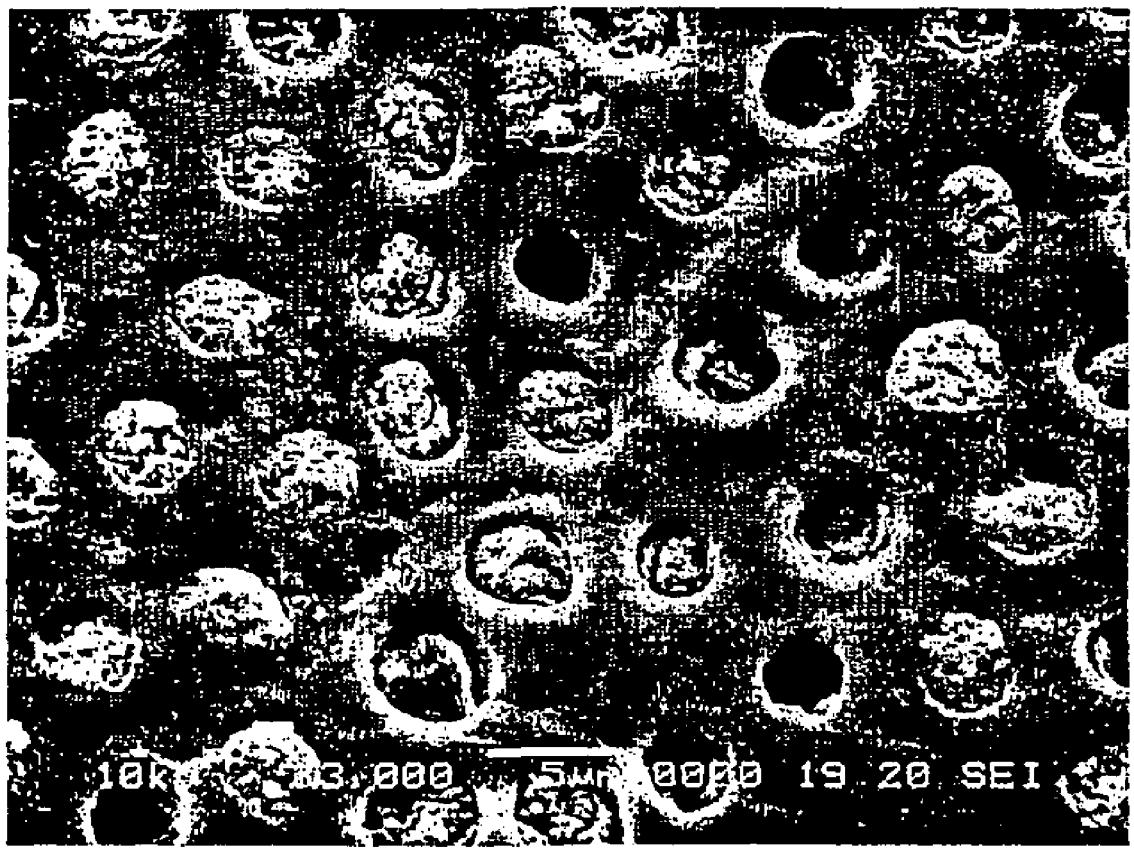

The invention relates to polymerisable multifunctional polymer composites and compositions, which are suitable for dental and medical applications, such as dental prostheses, filling materials, implants and the like. It also relates to a method for the manufacture of such multifunctional polymer composites and compositions, and to the use of said multifunctional polymer composites and compositions in dental and medical applications.

Polymeric particulate filler composites, such as those made from 2,2-bis-4-(2-hydroxy-3-methacryloxy)phenyl propane (BisGMA)-triethylene glycol dimethacrylate (TEGDMA) with inorganic fillers, are commonly used as tooth filling materials or in veneering of dental bridges. Shortcomings of such particulate filler composites, based on BisGMA-TEGDMA monomer systems, are their high volumetric shrinkage in polymerisation, inadequate wear resistance of the material and poor adhesive properties as substrates after being polymerised and aged. The latter shortcoming has made the repair of old composite fillings difficult by using dental adhesive techniques. In addition, laminating and veneering of a composite dental appliance is influenced negatively by poor adhesive properties of composite laminate layers. The problem of volumetric shrinkage relates also to dental adhesives, causing the polymerised adhesive film to detach from tooth structures and dentin tubulus.

The use of fibre-reinforced composites (FRC) in dental applications is based on mono- or dimethacrylate monomer systems to form a copolymer and/or a multiphase polymer matrix to the FRC. Adhering of a particulate filler composite to the FRC substrate is of great importance in clinical success of FRC restorations. The highly cross-linked dimethacrylate polymer matrix of FRCs has been shown to be an inadequate adhesive substrate for new polymer matrices when restoring the FRC. To overcome this problem, a multiphase polymer matrix, allowing formation of interpenetrating polymer network (IPN) bonding, has been introduced to the FRC. However, also these multiphase polymer matrices have the same problems with inadequate adhesive substrate properties. Some multiphase polymer matrix prepregs containing unspecified dendrimers have been disclosed in publication WO 99/45890.

The inadequate wear resistance of conventional dental filling composites relates to particle size, sizing of filler particles by coupling agents and type of the polymer matrix.

Hyperbranched polymers (HBP) and dendritic polymers are three-dimensional, highly ordered oligomeric and polymeric compounds which are synthesised starting from small initiator molecules by a reaction sequence which is continually repeated. These compounds differ significantly from conventional polymers used in dental materials. In a linear polymer, the chain is entangled due to intramolecular interactions, while HBPs and dendritic polymers are compact spherical molecules with many branches. Due to the spherical, highly branched structure, the HBPs and the dendritic polymers have a high number of functional end-groups located at the sphere of the structure, while a linear, unbranched polymer has only two functional end-groups. These unique properties make HBPs and dendritic polymers (also known as dendrimers) highly interesting in many applications.

HBPs and dendritic polymers are well known in the literature. U.S. Pat. No. 5,418,301 discloses a dendritic macromolecule of polyester type having a central initiator molecule or initiator polymer with one or more reactive hydroxyl groups (A). The groups (A) are under formation of an initial tree structure, bonded to reactive carboxyl groups (B) of a monomeric chain extender having the two reactive groups (A) and (B). The tree structure is optionally extended and further branched from the initiator molecule or initiator polymer by addition of further molecules of a monomeric chain extender by means of bonding between the reactive groups (A) and (B) thereof and it is thereafter optionally further extended by reaction with a chain stopper.

U.S. Pat. No. 5,834,118 teaches a hyperbranched polyester of a polyol with 3 to 10 reactive hydroxyl groups and an aromatic polycarboxylic anhydride with 2 to 4 carboxyl groups, each hydroxyl group of the polyol forming an ester linkage with one anhydride group of the polycarboxylic anhydride, and further glycidyl (meth)acrylate or allyl glycidyl ether forming ester linkages with the remaining carboxyl groups of the anhydride and free hydroxyl groups. Further, in the hyperbranched polyester, (meth)acrylic anhydride and/or an aliphatic carboxylic anhydride form ester linkages with the free hydroxyl groups.

A hyperbranched polymer having at least 6 terminal hydroxyl or carboxyl groups and a Carothers gel point lower than 1 is disclosed in WO 93/18079. The HBP is comprised of a nucleus and polyol and polycarboxy residues. The hyperbranched polymer is obtainable by starting with a nucleus compound containing at least one hydroxyl group as the nucleus and reacting it with a compound containing at least one anhydride group, then the resulting first generation acid-terminated addition product is reacted with a compound containing at least one epoxy group. In the second generation, the resulting first generation hydroxyl-terminated addition product is reacted with a compound containing at least one anhydride group, then the resulting second generation acid-terminated addition product is reacted with a compound containing at least one epoxy group resulting in a second generation hydroxyl-terminated addition product. At least one generation monomers are used which have at least one functional group besides the anhydride group or epoxy group.

U.S. Pat. No. 5,886,064 discloses a granular, polymerisable composition which contains at least one polymerisable monomer and/or oligomer and a polymerisation initiator and optionally an accelerator and at least 70 wt % of a filler with a particle size of 0,1-1,0 μm, and additionally 0.5 to 28 wt % of a dendrimer. Suitable dendrimers are propyleneimine dendrimers, polyether/polythioether dendrimers, polyester dendrimers, polyphenyleneamide dendrimers and polyphenylene ester dendrimers. Preferably the dendrimers have polymerisable terminal groups which are (meth)acrylic, allyl, styryl, vinyl, vinyloxy and/or vinylamine groups. Said composition becomes flowable under compressive or shear stress. The composition can be packed in a similar manner like amalgam and it is suitable as a dental material or for the production of a dental material. The high filler content with optimized polymerisable monomer/oligomer content ensures the formation of a homogeneous granular system.

In applications, such as implants, the rigidity of the construction corresponding to the modulus of the bone plays an important role in diminishing the stress formation to the inter-phase between the implant and bone. The currently used endosseus implants are typically made of titanium alloys or cobalt-chromium alloys with a flexural modulus considerably higher than that of bone. The mismatch in these properties can explain partly the loosening of e.g. hip prostheses after use for some years. The FRC comprises a group of materials with mechanical properties which can be tailor-made corresponding to the properties of bone. The FRC, made of high rigidity fibres of silica, carbon/graphite or glass, increases the modulus of the material. On the other hand, the polymer matrix of FRC is also responsible in tailoring of the mechanical properties of FRC. The dimethacrylate based polymers (e.g. BisGMA-TEGDMA systems) result in relatively low flexural modulus which can retain the modulus of the FRC at a low level compared to that of cortical bone.

An object of the invention is to provide polymerisable, multifunctional polymer composites and compositions suitable for dental and medical applications, particularly for applications like filling materials, dental technological constructions, dental and orthopedical implants, other medical implants and endoprostheses, tissue guiding materials, cell and tissue culture matrix, orthopedical prostheses, drug releasing matrix materials and the like.

A further object of the invention is to provide a method for the manufacture of said polymerisable multifunctional polymer composites and compositions and polymerisable multifunctional polymer composite prepregs.

A still further object of the invention is the use of said polymerisable multifunctional polymer composites and compositions and polymerisable multifunctional polymer composite prepregs in dental and medical applications.

The characteristic features of the polymerisable multifunctional polymer composites and compositions for dental and medical applications, of the method for the manufacture of said polymerisable multifunctional polymer composites and compositions and of the use of said polymerisable multifunctional polymer composites and compositions in dental and medical applications are stated in the claims.

It has been surprisingly found that the disadvantages of the materials according to the state of the art, used in dental and medical applications, can be avoided or significantly reduced by using the solution according to the invention. According to the invention, polymerisable multifunctional polymer composites and compositions comprising 1) a reactive dendrimer or a combination of reactive dendrimers with various molecular weights, 2) a reactive solvent or a combination of reactive solvents, and 3) a nanofiller or a combination of nanofillers of various size, preferably the particle size being <0.1 μm, are especially suitable for dental and medical applications.

The polymerisable multifunctional polymer composite or composition comprises a) 30-99 wt % monomers comprising 30-99 wt %, preferably 50-90 wt % and particularly preferably 60-80 wt % of a dendrimer or a combination of dendrimers and 1-70 wt %, preferably 1-50 wt % and particularly preferably 1-30 wt % of a reactive solvent or a combination of reactive solvents, and b) 0.1-70 wt %, preferably 30-70 wt % and particularly preferably 50-70 wt % of a nanofiller or a combination of nanofillers.

The reactive dendrimer is selected from the group consisting of acrylate or methacrylate functionalised multifunctional cross-linkers, such as those described in the patent U.S. Pat. No. 5,834,118. Suitable dendrimers and hyperbranched polymers are obtained by reacting an initiator molecule having one or more hydroxyl groups with aromatic polycarboxylic compounds in a selective manner to obtain a ordered structure. Dendrimers and hyperbranched polymers obtained by the reaction of amino-containing initiator molecules with vinyl cyanides can also be used, as well as dendrimers and hyperbranched polymers obtained from the reaction between an initiator molecule having one or more hydroxyl groups and a chain extender having one hydroxyl groups and at last two carboxyl group. Mixtures of these dendrimers and hyperbranched polymers are also suitable. Dendrimers and hyperbranched polymers having a spherical structure are preferred. In addition, 102 dendrimers and hyperbranched polymers of the $2^{nd}$ or higher genereration are particularly suitable. The generation is defined as the number of consecutive reactions necessary to obtain the desired structure. The dendrimers and hyperbranched polymers have terminal end groups, which are reactive and can take part in a chemical reaction. Possible terminal groups are hydroxyl, carboxyl or amino groups. Dendrimers and hyperbranched polymers with combinations of these groups are also possible. The terminal groups are further reacted with organic reactants, so that the end group is converted to a reactive, polymerizable terminal group. For the present invention, suitable polymerizable terminal groups in the dendrimers are acrylic, methacrylic, allylic or vinylic group, of which the preferred ones are allylic, methacrylic and acrylic groups. Particularly preferable dendrimers are methacrylate terminated dendrimers.

The synthesis of dendrimers and hyperbranched polymers having reactive polymerizable groups is performed according to the principles of commonly known reactions, between suitable monomeric reagents and the dendrimers, respectively the hyperbranched polymers. Particularly preferred monomeric reagents are methacrylic acid chloride, methacrylic acid and methacrylic anhydride for the reaction with hydroxyl terminal dendrimers and hyperbranched polymers, 2-hydroxy ethyl methacrylate, allyl glycidylether, glycidyl acrylate and glycidyl-methacrylate for the reaction with carboxyl terminated dendrimers and hyperbranched polymers, acryloyloxy ethyl methacrylate for the reaction with amino containing dendrimers.

The nanofiller, which acts as a filling substance is an organic, an inorganic or an organic-inorganic-hybrid compound. The nanofiller is a solid powder at room temperature with a particle size of less than 0.1 μm. The organic nanofiller is selected from a group consisting of a polymer chain, a cluster of polymer chains, a co-polymer of said polymers and the like, such as polymerized alkyl acrylate and/or alkyl methacrylate monomers. Preferably the organic nanofiller is a cluster of polymer chains of polymethyl methacrylate (PMMA) or a cluster of polymer chains of polyethyleneglykol dimethacrylate (PEG DMA). The organic nanofiller can be in the form of polymerised solid particles, which are partly dissolved by the dendrimer and the reactive solvent. Organic nanofiller polymers consisting of monomers such as alkyl methacrylates and alkyl dimethacrylates, alkyl acrylates and alkyl diacrylates and preferably methyl methacrylate, mixed with reactive solvents, form after polymerisation nanofillers, like clusters of polymer chains, between the dendrimers.

The inorganic nanofiller is selected from a group consisting of particles of aluminium oxide, silicates, glass fillers such as quartz and barium glass fillers, ceramic materials, silica gel (Si-gel) and titanium gel (Ti-gel). Preferable inorganic nanofillers, with regard to improved wear resistance of dental filling composites, are quartz and barium glass fillers.

The organic-inorganic-hybrid nanofiller is selected from the group consisting of polysilsesquioxanes, known as POSS monomers.

The reactive solvent acts in the forming of the organic nanofiller phase in polymerisation, as a carrier for the organic or inorganic nanofiller, and in the lowering of the viscosity of the dendrimer to obtain a useable resin. Thus compositions with high dendrimer concentrations can be obtained. The reactive solvent, suitably an acrylate or methacrylate monomer such as methyl methacrylate, ethyl methacrylate, butyl methacrylate, propyl methacrylate and preferably methyl methacrylate, after being polymerised, forms also an organic nanofiller.

The composition or composite may optionally comprise reinforcement, such as glass fibre, carbon/graphite fibre and polyethylene fibre, and other suitable additives known in the art, such as plasticizers, antioxidants, polymerisation inhibitors, accelerators and catalysts if required. Drug substances and anti-microbiological agents may also be incorporated into the polymer composition or composite, preferably in combination with Si-gel and Ti-gel fillers.

The method for the manufacture of a polymerisable multifunctional polymer composite or composition comprises following steps:

A monomer mixture is prepared. The monomer mixture contains 30-99 wt %, preferably 50-90 wt % and particularly preferably 60-80 wt % of a dendrimer or a mixture of dendrimers, and 1-70 wt %, preferably 1-50 wt % and particularly preferably 1-30 wt % of a reactive solvent or a mixture of reactive solvents. To this monomer mixture 0.1-70 wt %, preferably 30-70 wt % and particularly preferably 50-70 wt % of an inorganic, an organic or an organic-inorganic-hybrid nanofiller or a combination of said fillers is added. The reactive dendrimer(s) is mixed with the reactive solvent(s) and the nanofiller(s) is then added. The components are mixed at room temperature or at a slightly elevated temperature of 20-50° C. using any suitable mixing technique. A polymerisation initiator and an optional catalyst are added, 0.1-3 wt % of each, and other optional additives. The mixture is stored at a cool place, preferably at or below a temperature of 10° C. and in dark, in a tightly closed container in order to avoid evaporation of volatile components and polymerisation of the mixture. The mixture is left to stand for up to one day to ensure complete solvation and mixing of all components. A gel-like dendrimer mixture is obtained with a viscosity, which is workable in the planned application.

The obtained gel-like dendrimer mixture can be mixed with 60-98 wt % of an inert solvent, such as an alcohol, ketone, alkane or the like, and preferable ones are ethanol, methanol, acetone, hexane, cyclohexane or tetrahydrofuran, in order to obtain a curable dental adhesive or a dental coating.

In the manufacture of a prepreg with suitable reinforcement, such as fibre reinforcement, the impregnation of the fibres with the monomer mixture is carried out, followed by optional evaporation of volatile components. All other ingredients are also incorporated into the prepreg before evaporation. The viscosity of the dendrimer gel can be modified in order to keep the desired reinforcing material, like individual glass fibres, in the gel together in the thus obtained prepreg during the processing and shaping of the prepreg into the desired form. The viscosity of the gel can be modified by varying the quantities of organic and inorganic fillers, or optionally varying the IPN structure of the polymeric fillers.

Also colour pigments and other conventional additives can be used in order to achieve the desired outlook and aesthetics, for example the colour of the patient's teeth.

The dendrimer gel, monomer mixture, dental adhesive, dental coating and preperg are curable by using preferably blue light or by auto-polymerisation, but also other curing methods can be used depending on the application. All conventional promoters, such as camphorquinone with amine catalyst can be used.

In the manufacturing process of the multifunctional polymer composite from the above described dendrimer prepreg, the polymeric nanofillers are reactively processed from solvent monomers used in processing of the highly viscous dendrimer system. The reactive organic dendrimer reacts with the organic nanofiller and the polymer chains or cluster of polymer chains of the nanofiller which are either covalently bound to the dendrimers or bound via interpenetrating polymer network (IPN) mechanism to the dendrimers. The molecules are polymerised on molecular level within each other. In the case of an inorganic nanofiller, the reactive dendrimer reacts with the aid of or via a coupling agent(s) to yield a bond between the dendrimer and the coupling agent such as silanes or titanates, such as 3-(trimethoxysilyl)propyl methacrylate or titanium methacrylate triisopropoxide, or the filler particles are trapped physically into the spaces between the dendrimers. In a polymer composite comprising Si-gel or Ti-gel nanofillers, the fillers partially or totally penetrate into the spaces in the dendrimer structure. When an organic filler is used in the composite, a reactive solvent, preferably an acrylate or methacrylate monomer, polymerises with the dendrimer. After polymerisation the composition may be bonded to other resins either through free radical polymerisation of dendrimers or organic fillers or via formation of IPN.

When using the multifunctional polymer composite or composition according to the invention, problems related to inadequate adhesive properties of the substrate are solved. According to the invention, the introducing of a multifunctional monomer system results in large quantities of unreacted functional groups in the polymer matrix. The unreacted functional groups of the polymerised and aged filling composite or FRC construction are activated at the time when adhering new liquid composite material on the aged one. The polymerisation reaction forms adhesive covalent bonds between the multifunctional polymer matrix in the FRC and the newly applied composite material.

HBPs and dendrimers are particularly suitable in dental and medical applications. The spherical shape of the molecule gives favourable rheological properties, which are advantageous when manufacturing the FRC. As the spherical shape and size can be tailored by selecting HBPs and dendrimers of different sizes, is it possible to control the packaging of the individual components in the resin matrix used in the FRC. Further the interaction between the resin matrix and the fillers and reinforcements used in the FRCs can be enhanced by selecting a HBP or dendrimer with proper end-group functionality.

According to the invention, the wear resistance is improved by incorporating organic, inorganic, or organic-inorganic hybrid nanofiller particles into the intermolecular spaces between the dendrimer molecules. The size of the nanoscale fillers is selected according to the intermolecular space available between the dendrimer molecules. The surface of the fillers is functionalised in order to react with the functional groups of the outermost shell of the dendrimer molecules. The fillers are strongly adhered and nanomechanically trapped between the dendrimer molecules, which increases considerably the wear resistance of the particulate filler composite. The problems related to the use of current FRCs, such as high volumetric polymerisation contraction, can be solved by introducing hyperbranched or dendritic polymers into the FRCs. The use of multifunctional dendrimers instead of dimethacrylate monomers increases the mechanical properties of polymer matrix by extensively cross-linked nature of the polymer. The volumetric shrinkage in polymerisation, of the composites and compositions according to the present invention is remarkably low.

Nanofillers made from reactive solvent mixtures, used for lowering of viscosity of dendrimers have not been disclosed in prior art. Said nanofillers are particularly important and useful as they fill intermolecular spaces available between the dendrimer molecules. The dendrimer-nanofiller composites and compositions can be used as bulk material or as a polymer matrix of FRC. Applications of fibre-reinforced composite (FRC) bridges are possible with using fibers. Prior art discloses only dendrimer compositions with low concentrations of dendrimers. The present invention provides the use of a reactive solvent as a carrier/former of nanofillers, and as a modifier of viscosity of the dendrimer composition system before polymerisation, which results high concentrations of dendrimers in the final compositions.

The multifunctional polymer composites and compositions thus obtained are suitable for dental and medical applications, fling materials, with or without reinforcement, depending on the application. The multifunctional polymer composites and compositions according to the invention may be used as bulk materials or in the polymer matrix of fibre composites or particulate filler composites in applications, such as tooth filling composites, dental adhesives, dental applications, other dental technological constructions, dental and orthopedical implants, medical implants and endoprostheses, tissue guiding materials, cell and tissue culture matrix, orthopedical prostheses, drug releasing matrix materials and the like.

Following examples provide a better understanding of the present invention, however they are not be intended as limiting the scope thereof.

EXAMPLES

Examples 1-3

Manufacture of a Light Polymerisable Dendrimer Mixture

A hyperbranched polymer with methacrylic endgroups (HBP-1, dendrimer made from pentaerythritol, 1,2,4-benzenetricarboxylic anhydride, glycidyl methacrylate and methacrylic anhydride, prepared as described in patent U.S. Pat. No. 5,834,118), methyl methacrylate (MMA), camphorquinone (CQ) and 2-(N,N-dimethylamino)-ethyl methacrylate (DMAEMA) were weighted and mixed in 3 different weight ratios at room temperature. 3 mixtures were stored in a closed container in refrigerator at a temperature below 10° C. The mixtures were left to stand for one day to ensure complete mixing of the components. Disc shaped samples (diameter 5.5 mm, thickness 0.75 mm) were polymerised with blue light (400-520 nm) for 40 seconds. The degree of conversion was measured with a FTIR-spectrometer for 15 minutes after the beginning of polymerisation. The results are shown in Table 1.

TABLE 1

Degree of conversion (DC) of different multifunctional polymer composites.

| Example | HBP-1 (wt %) | MMA (wt %) | CQ (wt %) | DMAEMA (wt %) | DC (%) |
|---|---|---|---|---|---|
| 1. | 78.4 | 19.6 | 1.0 | 1.0 | 56.2 |
| 2. | 76.0 | 19.0 | 2.5 | 2.5 | 64.2 |
| 3. | 73.6 | 18.4 | 4.0 | 4.0 | 65.5 |

Example 4

Manufacture of a Multifunctional Dendrimer FRC Prepreg 50 wt % of dendrimer (HBP-1, dendrimer made from pentaerythritol, 1,2,4-benzenetricarboxylic anhydride, glycidyl methacrylate and methacrylic anhydride, prepared as described in patent U.S. Pat. No. 5,834,118), 50 wt % of reactive monomer solvent MMA and 1 wt % of a photoinitiator accelerator mixture of example 1 were mixed together. Bundles of silanized E-glassfiber rowings, coated with porous PMMA (prepared as described in the patent WO 96/25911) were dipped into the mixture for 5 minutes. The PMMA phase on the fiber was plasticised with the dendrimer mixture, and the dendrimer-MMA mixture further impregnated the fiber bundles. Air bubbles were removed by applying vacuum. After dipping, the prepreg was slightly heated, at a temperature of 50° C. for 30 minutes. During heating, MMA evaporated from the prepreg, so that the final photocurable prepreg consisted of mainly the HBP-1 dendrimer matrix and E-glass fibers. Prepregs with larger residual amounts of MMA can also be manufactured, and the amount of MMA can be controlled by variation of the evaporation time and temperature.

Optionally the prepreg can be coated with a PMMA-film in a last step, by dipping it quickly into a mixture of tetrahydrofuran and PMMA (90 wt % +10 wt %).

Example 5

Properties of FRC Made with Dendrimer Matrix

The mechanical properties of the dendrimer prepreg FRC having a MMA concentration of 20 wt %, manufactured as described in example 4, were measured after light curing and the results are shown in Table 2.

TABLE 2

Results of three-point bending test according to ISO 10477.

| Specimen/ Dendrimer prepreg | Flexural strength (MPa) | Flexural modulus (Gpa) |
|---|---|---|
| HBP-1 (pure polymer) | 85.3 ± 29.3 | 4.5 ± 0.7 |
| HBP-1 (24 vol % glassfiber) | 613.6 ± 44.1 | 13.8 ± 1.4 |

Examples 6-9

Effect of Concentration of Reactive Solvent Added on the Properties of Dendrimer FRC Prepreg The effect of MMA concentration on the mechanical properties of 4 dendrimer prepregs, manufactured as described in example 4 and light cured, is shown in Table 3.

TABLE 3

Results of mechanical properties as a function of MMA concentration.

| Example | Concentration of MMA | Flexural strength (MPa) | Flexural modulus (GPa) |
|---|---|---|---|
| 6. | 20 wt % | 613.6 | 13.8 |
| 7. | 30 wt % | 558.5 | 11.3 |
| 8. | 40 wt % | 525.0 | 12.0 |
| 9. | 50 wt % | 507.6 | 10.7 |

Example 10

Shear Bond Test for Polymer Adhesion Applied to ISO/TR 11405

The shear bonding between a dendrimer containing substrate and a commercial dental adhesive was measured according to ISO/TR 11405. A dendrimer mixture composed of 80 wt % of HBP-1, 20 wt % of MMA and 1 wt % of CQ was prepared and cured a) in a light curing oven for 15 minutes, and b) using a handcuring unit for 40 s. The polymerisation was done under a Mylar film in order to achieve a smooth substrate surface. The surface was then threated with a commercial restorative adhesive (Sinfony Activator) for 5 min and the adherend stub was polymerised for 15 minutes in a light curing oven. The results are presented in the following table 4.

TABLE 4

| Curing | Shear bond Shear bond test (MPa) |
|---|---|
| Light curing oven | 21.1 ± 7.9 |
| Handcuring | 16.7 ± 4.4 |

Example 11

Use of Dendrimer Prepreg in the Manufacture of a Dental Bridge

The manufacture of a fibre composite resin-bonded-bridge (RBB) does not require any tooth preparation by grinding like the manufacture of a conventional bridge. A RBB was made on a primary dental cast by pressing an unidirectional prepreg of example 4 against the abutment teeth surfaces after which the prepreg was light-cured. The strength of the bridge can be considerably increased by an optional possibility to twist the prepreg around the distal or mesial abutment. The polymerized unidirectional prepreg was then rebased with a layer of weave prepreg and light-cured. Optionally, the frame of the prepreg can be covered with another layer of weave prepreg. The pontic teeth of the RBB were made from tooth coloured dental composite resin. The RBB was luted to the etched enamel surface with normal dental luting cements.

Example 12

Use of a Dendrimer Mixture as a Dental Adhesive

A dendrimer mixture, manufactured as in example 1, containing 5 wt % of methacrylated-POSS organic-inorganic-hybrid nanofiller was added to 90 wt % of inert solvent ethanol. Freshly extracted tooth was bonded into shear bond sample jig and grinded to a roughness of FEPA 1000 grit under water cooling. Immediately after grinding, exposed dentin surface was etched with a phosphoric acid solution having a concentration of about 35 wt %. The etched dentin was then flushed away with water spray. The dentin surface was slightly dried with air and a low viscosity dendrimer dentin primer was delivered onto the dentin surface. The ethanol was then vaporized leaving a thin layer of the dendrimer mixture on the surface. The dentin surface was then treated with a slight airflow and the dendrimer film was polymerised with light. An adherend stub (Z 100, 3M) was polymerised onto the surface as described in example 4. Shear bond tests for tooth adhesion was the done according to ISO/TR 11405. After the shear bond test, the fracture was examined with scanning electron microscopy, which showed that the dendrimer mixture had filled the dentin tubulus without shrinkage. In FIG. 1 a scanning electron micrograph of dentin surface is presented.

Example 13

Use of a Dendrimer Mixture as a Dental Coating

A FRC-bridge core was manufactured using the dendrimer prepreg manufactured in example 4. After polymerisation of the FRC-bridge core, a veneering composite was used to build up the shape and colour of a teeth. The veneering composite was polymerised and a thin dendrimer layer coating was applied on the surface of the FRC-bridge. The dendrimer mixture described in example 12 was used. Tetrahydrofuran (THF) was used instead of ethanol in order to achieve a slight solvation of the FRC surface. THF was then evaporated from the dendrimer coating film, and the film was polymerised in a light curing oven in vacuum. A smooth scratch resistant coating was achieved.

Example 14

Volumetric Shrinkage Test of Manufactured FRC Compositions

The volumetric shrinkage was measured for three compositions, see Table 4. As a reference a composition based on bisGMA was used, which was compared with two compositions based on hyperbranched polymers HBP-1 and HBP-2. (HBP-1 is a dendrimer made from pentaerythritol, 1,2,4-benzenetricarboxylic anhydride, glycidyl methacrylate and methacrylic anhydride, HBP-2 is a dendrimer made from pentaerythritol, 1,2,4-benzenetricarboxylic anhydride, glycidyl methacrylate and acetic anhydride, both prepared as described in patent U.S. Pat. No. 5,834,118.) The volumetric shrinkage was measured according to ASTM 792. The FRC compositions were polymerised using a handcuring unit Optilux for 40 sec, additionally were duplicate samples postpolymerised using a LicuLite light curing oven for 15 min.

TABLE 5

| Composition | Metacrylated resin (wt %) | MMA (wt %) | CQ (wt %) | DMAEMA (wt %) | Volumetric shrinkage (%) |
|---|---|---|---|---|---|
| BisGMA[a] | 78.0 | 20.0 | 1.0 | 1.0 | 9.6 |
| BisGMA[b] | 78.0 | 20.0 | 1.0 | 1.0 | 9.3 |
| HBP-1[a] | 78.0 | 20.0 | 1.0 | 1.0 | 6.5 |
| HBP-1[b] | 78.0 | 20.0 | 1.0 | 1.0 | 5.8 |
| HBP-2[a] | 78.0 | 20.0 | 1.0 | 1.0 | 7.0 |
| HBP-2[b] | 78.0 | 20.0 | 1.0 | 1.0 | 6.5 |

[a] = polymerised with handcuring unit Optilux 40 sec and postpolymerisation in a LicuLite light curing oven for 15 min
[b] = polymerised with handcuring unit Optilux 40 sec

Example 15

Density of Manufactured FRC Compositions

The density was measured for three compositions, see Table 6. As a reference a composition based on bisGMA was used, which was compared with two compositions based on hyperbranched polymers HBP-1 and HBP-2. (HBP-1 is a dendrimer made from pentaerythritol, 1,2,4-benzenetricarboxylic anhydride, glycidyl methacrylate and methacrylic anhydride, HBP-2 is a dendrimer made from pentaerythritol, 1,2,4-benzenetricarboxylic anhydride, glycidyl methacrylate and acetic anhydride, both prepared as described in patent U.S. Pat. No. 5,834,118.) The density was measured according to ASTM 792. The FRC compositions were polymerised using a handcuring unit Optilux for 40 sec, additionally were duplicate samples postpolymerised using a LicuLite light curing oven for 15 min.

TABLE 6

| Composition | Metacrylated Resin (wt %) | MMA (wt %) | CQ (wt %) | DMAEMA (wt %) | Density (g/mm$^3$) |
|---|---|---|---|---|---|
| BisGMA[a] | 78.0 | 20.0 | 1.0 | 1.0 | 1.211 |
| BisGMA[b] | 78.0 | 20.0 | 1.0 | 1.0 | 1.207 |
| HBP-1[a] | 78.0 | 20.0 | 1.0 | 1.0 | 1.277 |
| HBP-1[b] | 78.0 | 20.0 | 1.0 | 1.0 | 1.267 |
| HBP-2[a] | 78.0 | 20.0 | 1.0 | 1.0 | 1.263 |
| HBP-2[b] | 78.0 | 20.0 | 1.0 | 1.0 | 1.257 |

[a] = polymerised with handcuring unit Optilux 40 sec and postpolymerisation in a LicuLite light curing oven for 15 min.
[b] = polymerised with handcuring unit Optilux 40 sec Example 16

Effect of Photopolymerisation Time on Degree of Conversion

The degree of conversion for a FRC composition, prepared from HBP-1 as in example 1, was measured by FT-IR spectroscopy, as the ratio of the height for the C=C peak at 1638 cm 1, normalised against the aromatic C=C peak at 1582 cm −1. The polymerisation was done using Optilux handcuring unit for 40, 60 and 120 sec, see Table 7.

TABLE 7

| Curing time | Degree of cure |
|---|---|
| 40 sec | 56.8 |
| 60 sec | 57.4 |
| 120 sec | 58.6 |

The invention claimed is:

1. A method for the manufacture of a polymerisable multifunctional polymer composition, comprising the steps of:
  (a) preparing a monomer mixture by mixing 30-99 wt % of a methacrylate terminated dendrimer(s) with 1-70 wt % of a reactive solvent(s);
  (b) adding 30-99 wt % of the obtained monomer mixture, 0.1-70 wt % of a nanofiller(s) with a particle size of less than 0.1 μm, the nanofiller being an organic nanofiller or organic-inorganic-hybrid nanofiller, and forming a nanofiller phase in polymerisation, 0.1-3 wt % of a polymerisation initiator, an optional catalyst, in an amount of 0.1-3 wt %, and optional additives;
  (c) mixing the added monomer mixture, the nanofiller(s), the polymerisation initiator, optional catalyst, and optional additives at a temperature of 20-50° C.; and
  (d) mixing the obtained mixture of step (c) with 60-98% of an inert solvent selected from the group consisting of an alcohol, a ketone, an alkane, and tetrahydrofuran to obtain a dental adhesive or dental coating.

2. The method according to claim 1 for the manufacture of a polymerisable multifunctional polymer composition, wherein,
  50-90 wt % of a methacrylate terminated dendrimer(s) is mixed with 1-50 wt % of a reactive solvent(s) to form the monomer mixture, and
  30-70 wt % of a nanofiller(s) is added to the monomer mixture.

3. The method according to claim 1 for the manufacture of a polymerisable multifunctional polymer composition, wherein,
  60-80 wt % of a dendrimer(s) is mixed with 1-30 wt % of a reactive solvent(s) to form the monomer mixture, and
  50-70 wt % of a nanofiller(s) is added to the monomer mixture.

4. The method according to claim 1 for the manufacture of a polymerisable multifunctional polymer composition, wherein the nanofiller is a solid powder.

5. The method according to claim 1 for the manufacture of a polymerisable multifunctional polymer composition, wherein the organic nanofiller is selected from the group consisting of a polymer chain, a cluster of polymer chains, and a co-polymer of said polymers and the inorganic-organic hybrid filler is selected from the group consisting of polysilsesquioxanes.

6. The method according to claim 1 for the manufacture of a polymerisable multifunctional polymer composition, wherein the organic nanofiller is a cluster of polymer chains of polymethyl methacrylate (PMMA) or a cluster of polymer chains of polyethyleneglycol dimethacrylate (PEG DMA).

7. The method according to claim 1 for the manufacture of a polymerisable multifunctional polymer composition, wherein the reactive solvent is an acrylate or methacrylate monomer.

8. The method according to claim 1 for the manufacture of a polymerisable multifunctional polymer composition, wherein the reactive solvent is methyl methacrylate, ethyl methacrylate, butyl methacrylate or propyl methacrylate.

9. The method according to claim 1 for the manufacture of a polymerisable multifunctional polymer composition, wherein, the optional additives are selected from the group consisting of reinforcement additives, plasticizers, antioxidants, drug substances, anti-microbiological agents, colourants, polymerization initiators and catalysts.

10. The method according to claim 1 for the manufacture of a polymerisable multifunctional polymer composition, wherein the optional additives are selected from the group consisting of reinforcement additives, plasticizers, antioxidants, drug substances, anti-microbiological agents and colourants.

11. A method for the manufacture of a polymerisable multifunctional polymer composition, comprising the steps of:
  (a) preparing a monomer mixture by mixing 30-99 wt % of a methacrylate terminated dendrimer(s) with 1-70 wt % of a reactive solvent (s);
  (b) adding 30-99 wt % of the obtained monomer mixture, 0.1-70 wt % of a nanofiller(s) with a particle size of less than 0.1 μm, the nanofiller being an organic nanofiller or organic-inorganic-hybrid nanofiller, and forming a nanofiller phase in polymerisation,0.1-3 wt % of a polymerisation initiator, an optional catalyst, in an amount of 0.1-3 wt %, and optional additives;
  (c) mixing the added monomer mixture, the nanofiller(s), the polymerisation initiator, optional catalyst, and optional additives at a temperature of 20-50° C. to form a composition; and (d) mixing the obtained mixture of (c) with 60-98 wt % of an inert solvent selected from alcohol, ketone, and alkane.

12. The method according to claim 5 the manufacture of a polymerizable multifunctional polymer composition, wherein the organic nanofiller is selected from the group consisting of polymerized alkyl acrylate, polymerized alkyl methacrylate, polymerized alkyl acrylate with alkyl methacrylate, polymerized alkyl dimethacrylates, and polymerized alkyl diacrylates monomers.

13. The method according to claim 9 for the manufacture of a polymerizable multifunctional polymer composition, wherein the reinforcement additive is selected from the group consisting of glass fibre, carbon/graphite fibre and polyethylene fibre.

14. The method according to claim 10 for the manufacture of a polymerizable multifunctional polymer composition, wherein the reinforcement additive is selected from the group consisting of glass fibre, carbon/graphite fibre and polyethylene fibre.

15. The method according to claim 1 for the manufacture of a polymerizable multifunctional polymer composition, wherein the inert solvent is selected from the group consisting of ethanol, methanol, acetone, hexane, cyclohexane and tetrahydrofuran.

* * * * *